(12) United States Patent
Bichler et al.

(10) Patent No.: US 11,112,861 B2
(45) Date of Patent: Sep. 7, 2021

(54) DETERMINATION OF A SPATIAL ORIENTATION

(71) Applicant: Robert Bosch GmbH, Stuttgart (DE)

(72) Inventors: Rudolf Bichler, Reutlingen (DE);
Amithash Kankanallu Jagadish, Leonberg (DE); Markus Dihlmann, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 170 days.

(21) Appl. No.: 16/492,193

(22) PCT Filed: Feb. 1, 2018

(86) PCT No.: PCT/EP2018/052484
§ 371 (c)(1),
(2) Date: Sep. 9, 2019

(87) PCT Pub. No.: WO2018/162152
PCT Pub. Date: Sep. 13, 2018

(65) Prior Publication Data
US 2021/0141447 A1    May 13, 2021

(30) Foreign Application Priority Data
Mar. 8, 2017  (DE) .......................... 102017203755.5

(51) Int. Cl.
*G06F 3/01* (2006.01)
*G06F 3/0346* (2013.01)
*G01C 21/12* (2006.01)

(52) U.S. Cl.
CPC ............. *G06F 3/012* (2013.01); *G01C 21/12* (2013.01); *G06F 3/0346* (2013.01)

(58) Field of Classification Search
CPC . G06F 3/01; G06F 3/012; G06F 3/346; G06F 3/3544; G01C 21/12; A61B 5/1114; A61B 5/1121; A61B 5/6803
See application file for complete search history.

(56) References Cited

U.S. PATENT DOCUMENTS 5,645,077 A * 7/1997 Foxlin ................... A61B 5/1114
600/587
5,991,085 A * 11/1999 Rallison ............... G02B 27/017
345/8

(Continued)

FOREIGN PATENT DOCUMENTS

| JP | 2017191474 A | 10/2017 |
|---|---|---|
| JP | 2017203760 A | 11/2017 |

OTHER PUBLICATIONS

International Search Report for PCT/EP2018/052484, dated Aug. 28, 2018.

*Primary Examiner* — Mihir K Rayan
(74) *Attorney, Agent, or Firm* — Norton Rose Fulbright US LLP; Elizabeth Tretter

(57) ABSTRACT

A method for determining the spatial orientation of an object encompasses the steps of detecting a rotational speed of the object with the aid of a first sensor; determining an estimated value for the spatial orientation of the object based on the detected rotational speed and a starting value for the spatial orientation; detecting the acceleration $a_{meas}$ acting on the object with the aid of a second sensor; determining the acceleration component of the detected acceleration $a_{meas}$ resulting from the rotational movement, based on the detected rotational speed and a given distance of the second sensor from the rotational axis of the rotational movement; determining the acceleration component $a_{grav}$ of the detected acceleration $a_{meas}$ resulting from the gravity; and correcting the estimated value for the spatial orientation, taking into (Continued)

account the acceleration component $a_{grav}$ resulting from the gravity.

11 Claims, 3 Drawing Sheets

(56) References Cited

U.S. PATENT DOCUMENTS

| | | | | |
|---|---|---|---|---|
| 6,474,159 | B1* | 11/2002 | Foxlin | G01C 21/12 |
| | | | | 73/488 |
| D701,206 | S | 3/2014 | Luckey et al. | |
| 10,248,191 | B2* | 4/2019 | McGee | G02B 27/0093 |
| 10,838,203 | B2* | 11/2020 | Franklin | G02B 27/0093 |
| 2002/0060633 | A1* | 5/2002 | Crisco, III | A61B 5/1121 |
| | | | | 340/669 |
| 2002/0194914 | A1 | 12/2002 | Foxlin et al. | |
| 2009/0322679 | A1* | 12/2009 | Sato | A63F 13/98 |
| | | | | 345/158 |
| 2009/0326857 | A1* | 12/2009 | Mathews | G06F 3/038 |
| | | | | 702/141 |
| 2012/0278024 | A1* | 11/2012 | Lee | G01P 21/00 |
| | | | | 702/87 |
| 2014/0184509 | A1* | 7/2014 | Mathews | G06F 3/0383 |
| | | | | 345/163 |

* cited by examiner

DETERMINATION OF A SPATIAL ORIENTATION

FIELD OF THE INVENTION

The present invention relates to the determination of a spatial orientation. In particular, the present invention relates to the determination of the spatial orientation of a virtual reality (VR) device mounted on the head of a user.

BACKGROUND INFORMATION

For presenting a virtual situation, a user is provided with sensory stimuli that preferably consistently match the virtual situation. For this purpose, a visual or acoustic VR device ("headset") that is mounted on the head of the user, and that includes a visual display device and/or an acoustic output device, may be provided.

US D 701 206 S1 provides such a VR device. When the user moves his/her head, the user's perspective on the virtual situation that is shown to the user with the aid of the display device should follow the movement of his/her head. For this purpose, the spatial orientation of the VR device in space should be determined preferably quickly and accurately. A gyroscope that measures a rotation rate about one or multiple axes is generally used for this purpose. The orientation may be determined by integration of the rotation rate over time.

However, in particular inexpensive gyroscopes are subject to a certain measuring inaccuracy. To compensate for inaccuracies or errors, the direction of the acceleration of gravity may be determined as a reference with the aid of an accelerometer. Since the accelerometer usually is not situated exactly on the rotational axis of the head, for example twisting of the head about the longitudinal axis can be determined only when a rotation about the vertical axis is actually taking place.

SUMMARY

An object underlying the present invention is to provide an improved technique for determining the spatial orientation of a VR device.

A method for determining the spatial orientation of an object encompasses the steps of detecting a rotational speed of the object with the aid of a first sensor; determining an estimated value for the spatial orientation of the object based on the detected rotational speed and a starting value for the spatial orientation; detecting acceleration $a_{meas}$ acting on the object with the aid of a second sensor; determining the acceleration component of detected acceleration $a_{meas}$ resulting from the rotational movement, based on the detected rotational speed and a given distance of the second sensor from the rotational axis of the rotational movement; determining acceleration component $a_{grav}$ of detected acceleration $a_{meas}$ resulting from the gravity; and correcting the estimated value for the spatial orientation, taking into account acceleration component $a_{grav}$ resulting from the gravity.

By use of the described method, in particular a long-term drift or a measuring error of the first sensor may be compensated for in an improved manner. The spatial orientation in space may thus be determined quickly and accurately. The use of a low pass filter for smoothing measured acceleration values may be avoided. The spatial orientation determined with the aid of the method may thus be present with reduced latency. The method is particularly suited for use on a VR device, which requires a low-latency and accurate information concerning the rotatory orientation in order to produce a convincing VR effect.

The method is preferably run through iteratively, in that in each pass of the method, the corrected estimated value for the spatial orientation of the object from the preceding pass is taken as the starting value for the spatial orientation. When used in conjunction with a VR device, the method may be carried out at a frequency of several 1000 Hz, for example. By feedback of the determined orientation into the orientation determination of a subsequent pass, an overall improved accuracy of the determined orientation may be achieved.

The determination of the estimated value for the spatial orientation may include integration of the detected rotational speed over time. In particular, a numeral integration is preferred. This may be implemented in a particularly efficient manner when the method is run through iteratively in equal time intervals.

The translational components are based on a circular path that the sensor may describe about the rotational axis. In one specific embodiment, the translational components include a centripetal acceleration. The translational components may also include a tangential acceleration. At least one tangential acceleration component $a_{tan}$ and at least one centripetal acceleration component $a_{cent}$ may be ascertained within the scope of determining the acceleration component resulting from the rotational movement. The tangential acceleration may occur in particular at the beginning and at the end of a rotational movement. The centripetal acceleration may act in particular during a rotational movement, and its magnitude may be a function of the angular velocity of the rotation about the rotational axis and its direction from a rotational axis and a rotation angle.

The direction of the gravity may be ascertained within the scope of determining acceleration component $a_{grav}$ resulting from the gravity. The direction of acceleration component $a_{grav}$ may be taken into account in correcting the estimated value for the spatial orientation. A computer program product includes program code means for carrying out the above-described method when the computer program product runs on a processing device or is stored on a computer-readable data medium.

Portions of the method may be carried out in particular with the aid of a processing device, which may include a programmable microcomputer or microcontroller. Advantages or features of the method, of the computer program product, of a device that includes such a processing device, and of a system that includes the device may be correspondingly based on the respective other subject matter.

A device for determining the spatial orientation of an object includes a first sensor for detecting the rotational speed of the object; a second sensor for detecting acceleration $a_{meas}$ acting on the object, and a processing device. The processing device is configured for determining an estimated value for the spatial orientation of the object, based on the detected rotational speed and a starting value for the spatial orientation; determining the acceleration component of detected acceleration $a_{meas}$ resulting from the rotational movement, based on a given distance of the second sensor from the rotational axis of the rotational movement; determining acceleration component $a_{grav}$ of detected acceleration $a_{meas}$ resulting from the gravity; and correcting the estimated value for the spatial orientation, taking into account acceleration component $a_{grav}$ resulting from the gravity.

The device may generally be used for determining the spatial orientation of any object. Examples of objects include a hand tool, in particular a hand-held power tool, a motor vehicle, or a mobile computer. As mentioned, the processing device is preferably configured for carrying out at least portions of the above-described method.

In addition, it is preferred that one of the sensors is encompassed by a micromechanical system. The micromechanical system (also microelectromechanical system or micromachine) is generally designed with semiconductor technology, and uses components whose smallest dimensions are typically in the micron range. Such a sensor generally includes a micromechanical test mass that is movably suspended, sensors for sampling the movement of the test mass, and an evaluation circuit for determining the desired variable based on the determined movement. Such sensors may be cost-efficient. Measurement inaccuracies or a long-term drift of such a sensor may be better compensated for by the described processing.

The first sensor may be a one-axis, two-axis, or three-axis micromechanical gyrosensor. The second sensor may be a one-axis, two-axis, or three-axis micromechanical acceleration sensor.

A VR device includes a fastening device fastening to the head of a user, a visual or acoustic output device, and the above-described device. In this way, an adaptation of stimuli to a determined spatial orientation with the aid of the visual or acoustic output device may be carried out in an improved manner. The user may thus form a greatly improved realistic impression of the information presented.

In another preferred specific embodiment, the fastening device is adjustable, and a sampling device is provided for determining the distance of the second sensor from the rotational axis, based on an adjustment state of the fastening device. The method may thus be automatically adapted to different head sizes of various users in an improved manner. The accuracy of the determined spatial orientation may thus be increased.

DETAILED DESCRIPTION

Figure 1:
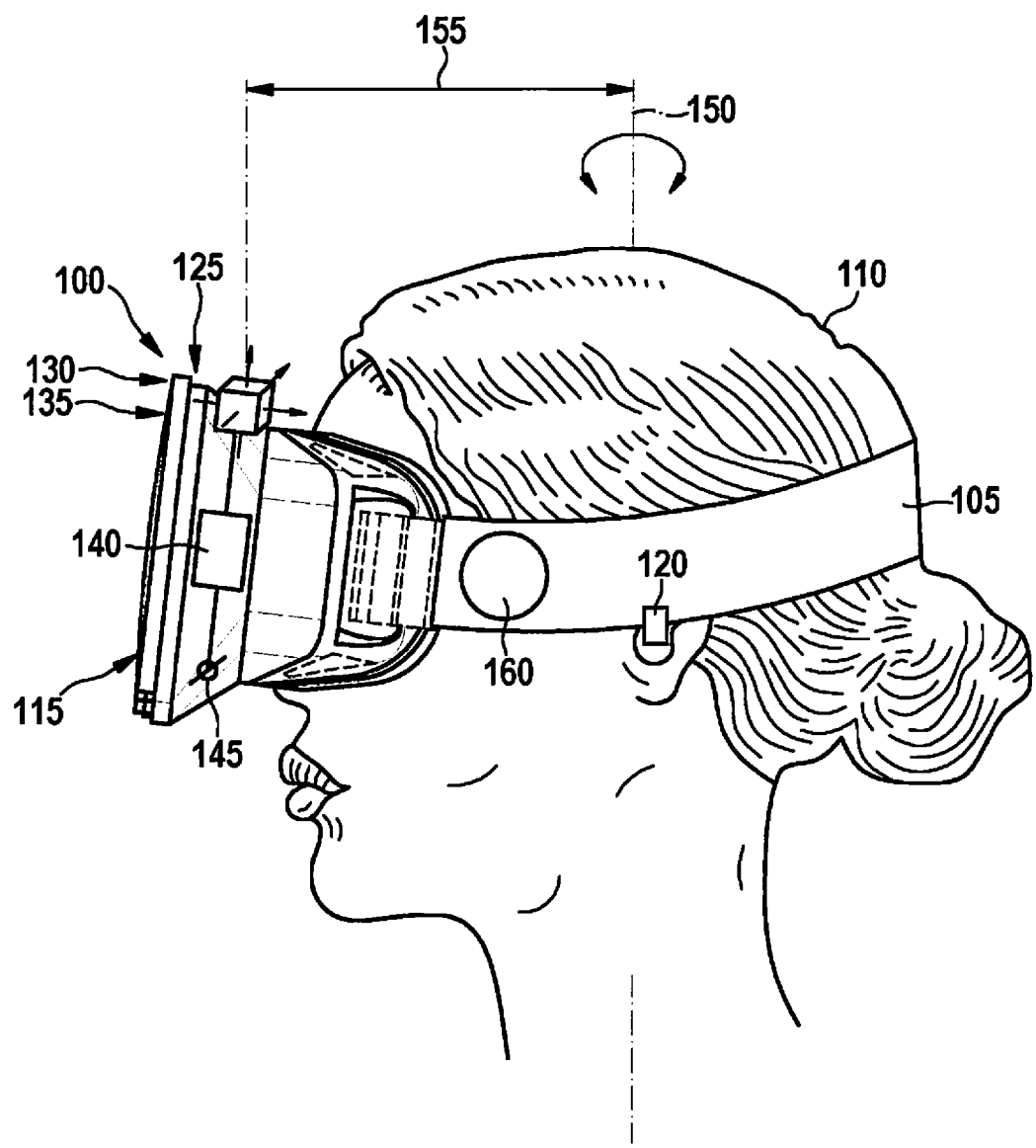
FIG. 1 shows a VR device for fastening to the head of a user.

FIG. 1 shows a VR device 100 that is mounted on the head of a user 110 with the aid of a fastening device 105. The VR device preferably includes a visual output device 115 and/or an acoustic output device 120. With the aid of output devices 115, 120, stimuli may be presented to user 110 that give him/her the impression of a generated, i.e., virtual, reality. For this purpose, the stimuli are to be controlled as a function of a spatial orientation of the head of user 110.

For this purpose, a device 125 that preferably includes a first sensor 130 for determining a rotational speed and a second sensor 135 for determining an acceleration is provided on VR device 100. In addition, a processing device 140 and preferably an interface 145 for providing the determined spatial orientation are provided. One or both sensors 130, 135 may in particular be designed as micromechanical sensor(s). In the illustrated specific embodiment, the two sensors 130, 135 are integrated with one another as an example. A first approximation for the spatial orientation of VR device 100 or device 125 may be determined based solely on first sensor 130. However, since first sensor 130 measures only accelerations, i.e., a change in the spatial orientation, an initialization must take place. This initialization may take place, for example, with regard to the direction of the acceleration of gravity, which may be determined with the aid of second sensor 135 when device 125 is at rest. The adjustment to the direction of the acceleration of gravity may also be used to compensate for measuring errors or a long-term drift of first sensor 130.

However, if user 110 turns his/her head, for example about a vertical axis 150, forces may thus act on second sensor 135 that occasionally distort the determination of the direction of the acceleration of gravity. It is proposed to compensate for this distortion. For this purpose, it may be helpful to know a distance 155 between second sensor 135 and rotational axis 150. In one specific embodiment, this distance 155 may be estimated or set. In another specific embodiment, user 110 may specify distance 155 him/herself. In the illustrated, preferred specific embodiment, fastening device 105 has an adjustable design to allow the VR device to be mounted on different sizes of heads of various users 110. Distance 155 may be a function of the size of the head of user 110. A sampling device 160 may be provided to sample adjustable fastening device 105 and thus provide a measure for the magnitude of distance 155. Distance 155 is then preferably further processed with the aid of processing device 140.

Figure 2:
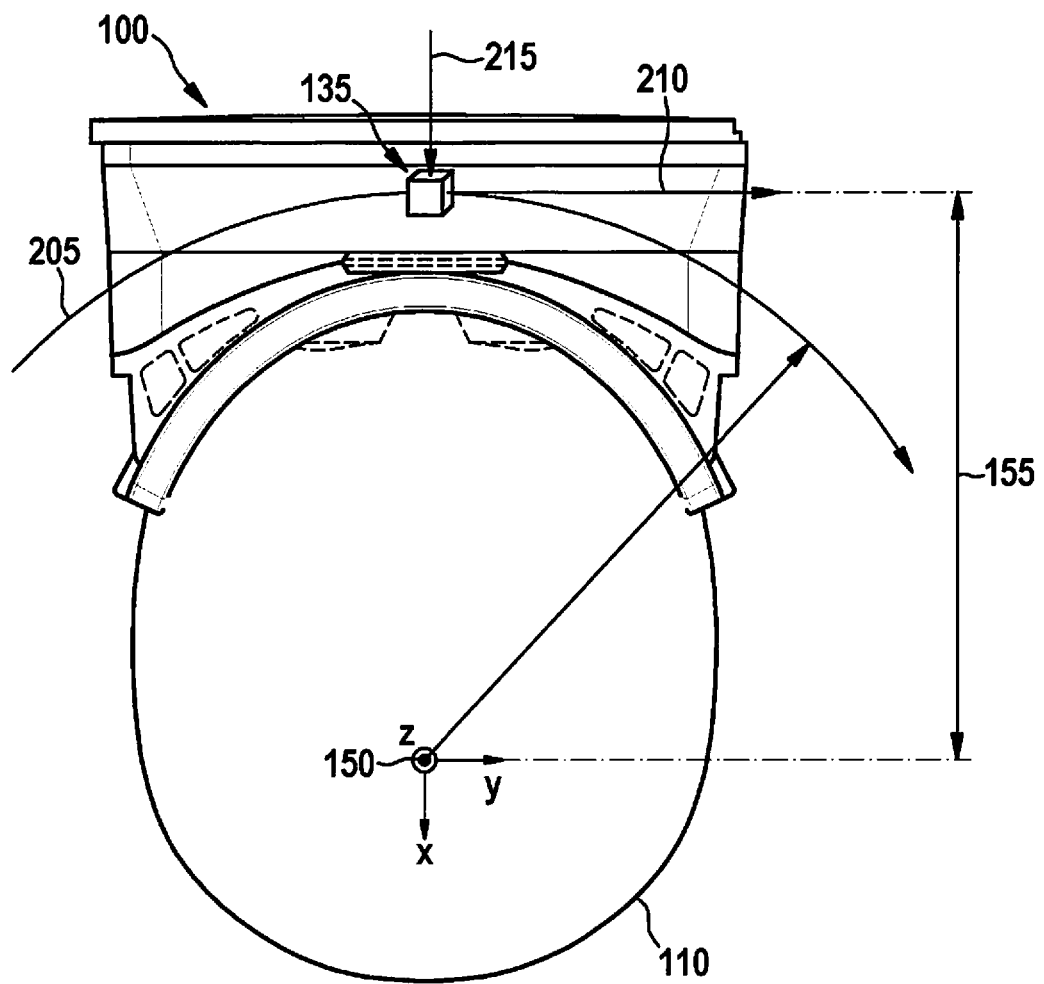
FIG. 2 shows a schematic illustration of translational accelerations that act due to a rotational speed.

FIG. 2 shows a schematic illustration of accelerations that act on second sensor 135 from FIG. 1 due to a rotational acceleration. The head of person 110 and VR device 100 are indicated in a top view in FIG. 2. A three-dimensional Cartesian coordinate system is indicated for orientation. The z axis extends out of the plane of the illustration, toward the observer, and coincides, for example, with vertical axis 150 from FIG. 1.

When user 110 turns his/her head about vertical axis 150, second sensor 135 moves on an approximate circular path 205 about rotational axis 150. If the rotational speed changes, for example at the beginning or toward the end of the rotational movement, a tangential acceleration 210 acts on second sensor 135. In addition, a centripetal acceleration 215 pointing toward rotational axis 150 acts on second sensor 135 as long as it is moved along circular path 205. During the turning operation of the head of user 110, the direction of the acceleration of gravity, which correctly extends opposite the z direction in FIG. 2, may be deflected in the direction of tangential acceleration 210 or of centripetal acceleration 215. Magnitudes of the accelerations are a function of distance 155 between second sensor 135 and rotational axis 150, and also of magnitudes of the rotational movement or rotational speed about rotational axis 150.

Figure 3:
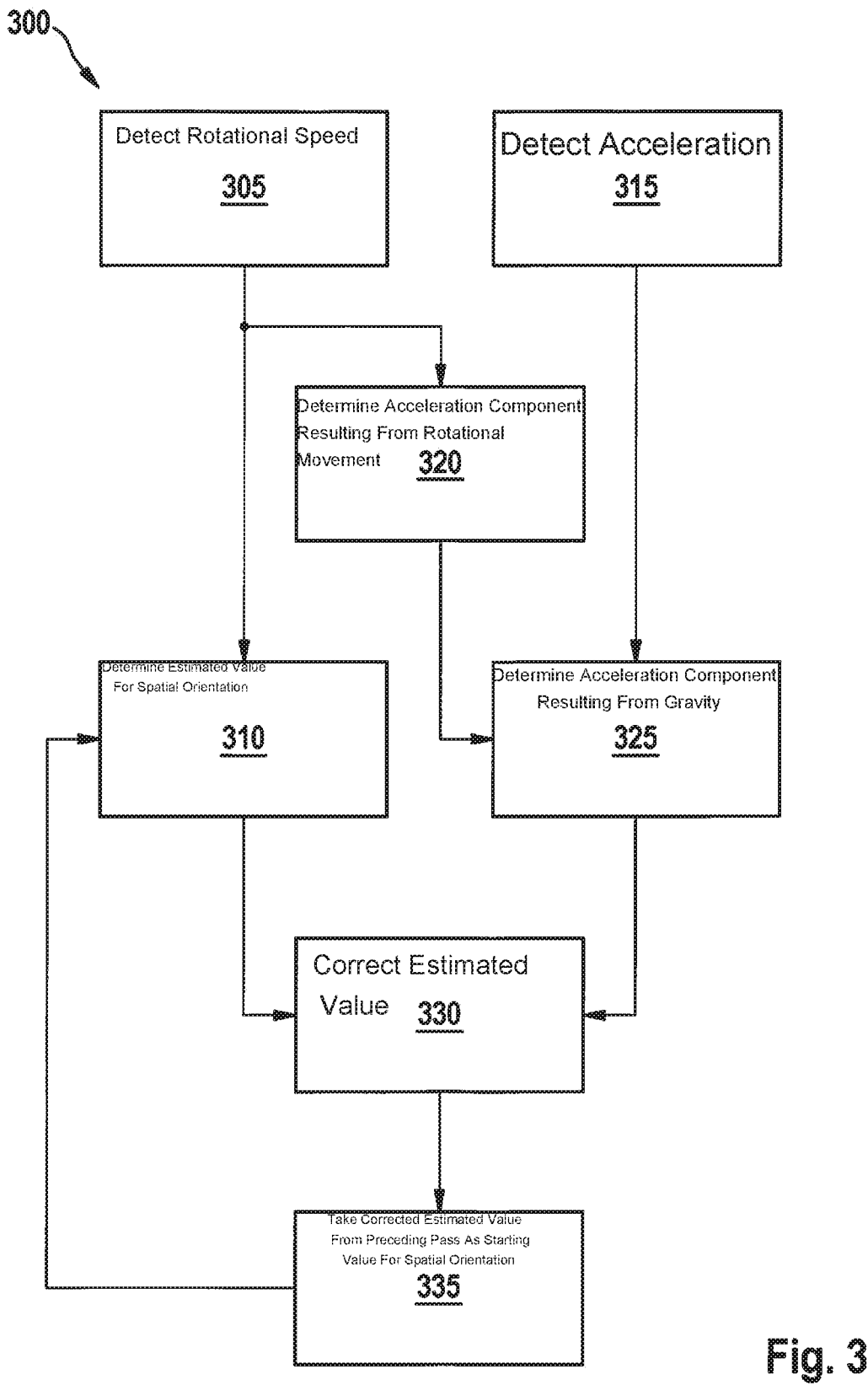
FIG. 3 illustrates a flow chart of a method for determining a spatial orientation.

FIG. 3 shows a flow chart of a method 300 for determining a spatial orientation. The method 300 may be used in particular in conjunction with device 125 from FIG. 1. Device 125 does not necessarily have to be part of a VR device 100.

A rotational speed is sampled with the aid of first sensor 130, for example, in a step 305. Based on the sampled values, the spatial orientation of first sensor 130 or of system 125, 100 that encompasses it is determined in a step 310. For this purpose, the determined rotational speed may in particular be integrated over time.

The acceleration of second sensor 135 or of system 125, 100 that encompasses it is determined in a step 315, preferably at or near the same time as step 305, with the aid of second sensor 135, for example. If no rotation of second sensor 135 is taking place, the direction of the sampled acceleration corresponds to the direction of Earth's gravity. However, if second sensor 135 is in rotation, translational forces must be determined in order to isolate the actual direction of the acceleration of gravity from the measured value.

For this purpose, the translational components, in particular tangential acceleration 210 and centripetal acceleration 215 (see FIG. 2), are preferably determined in a step 320. The tangential acceleration may be expressed as follows:

$$a_{tan,k} = \frac{d}{dt}\omega_k \times r_k \quad \text{(equation 1)}$$

where:
$a_{tan}$=tangential acceleration
ω=angular velocity
t=time
rt=distance 155.

Index k stands for a pass of method 300. A preceding pass has index k−1, and a subsequent pass has index k+1.

Similarly, the centripetal acceleration may be given as follows:

$$a_{cent,k} = \omega_k \times \omega_k \times r_k \quad \text{(equation 2)}$$

where:
$a_{cent}$=centripetal acceleration.

The time derivative of the angular velocity used in equation 1 is preferably determined as follows:

$$\frac{d}{dt}\omega_k = \frac{\omega_{k+1} - \omega_k}{\Delta t} \quad \text{(equation 3)}$$

where:
Δ[t]=time interval between steps k and (k+1).

With knowledge of translational components 210, 215, the direction of the acceleration of gravity may then be determined in a step 325, based on the sampled translational acceleration, as follows:

$$a_{grav,k} = a_{meas} - (a_{tan,k} + a_{cent,k}) \quad \text{(equation 4)}$$

where:
$a_{meas}$=measured translational (linear) acceleration

The spatial orientation previously determined in step 310 may now be corrected in a step 330, using the determined acceleration of gravity. The corrected spatial orientation is preferably provided in a step 335, for example with the aid of interface 145.

The stated determinations are generally carried out in three dimensions. The processing may take place in particular with the aid of linear algebra or vectors and matrices. Method 300 may be implemented on a programmable microcomputer, for example, with reasonable effort.

What is claimed is:

1. A method for determining a spatial orientation of an object, the method comprising: detecting a rotational speed of the object with a first sensor; determining an estimated value for the spatial orientation of the object based on the detected rotational speed and a starting value for the spatial orientation; detecting an acceleration component of the detected acceleration resulting from a rotational movement of the object, based on the detected rotational speed and a given distance of the second sensor from a rotational axis of the rotational movement; determining an acceleration component of the detected acceleration resulting from gravity; correcting the estimated value for the spatial orientation, taking into account the acceleration component resulting from gravity; and determining the distance of the second sensor from the rotational axis, based on an adjustment state of a fastening device, wherein the fastening device is adjustable, and wherein the fastening device is for fastening to a head of a user.

2. The method as recited in claim 1, wherein the method is run through iteratively, in that in each pass of the method, the corrected estimated value for the spatial orientation of the object from a preceding pass of the method is taken as the starting value for the spatial orientation.

3. The method as recited in claim 1, wherein the determining of the estimated value for the spatial orientation includes integrating the detected rotational speed over time.

4. The method as recited in claim 1, wherein the determining of the acceleration component of the detected acceleration resulting from the rotational movement of the object includes ascertaining at least one tangential acceleration component and at least one centripetal acceleration component.

5. The method as recited in claim 1, wherein the determining of the acceleration component of the detected acceleration resulting from gravity includes ascertaining a direction of gravity.

6. The method as recited in claim 1, wherein a direction of the acceleration component resulting from gravity is taken into account in the correcting of the estimated value for the spatial orientation.

7. A non-transitory computer readable medium having a computer program, which is executable by a processor, comprising: a program code arrangement having program code for determining a spatial orientation of an object, by performing the following: detecting a rotational speed of the object with a first sensor; determining an estimated value for the spatial orientation of the object based on the detected rotational speed and a starting value for the spatial orientation; detecting an acceleration acting on the object with a second sensor; determining an acceleration component of the detected acceleration resulting from a rotational movement of the object, based on the detected rotational speed and a given distance of the second sensor from a rotational axis of the rotational movement; determining an acceleration component of the detected acceleration resulting from gravity; and correcting the estimated value for the spatial orientation, taking into account the acceleration component resulting from gravity; and determining the distance of the second sensor from the rotational axis, based on an adjustment state of a fastening device, wherein the fastening device is adjustable, and wherein the fastening device is for fastening to a head of a user.

8. A device for determining a spatial orientation of an object, comprising: a first sensor for detecting a rotational speed of the object; a second sensor for detecting an acceleration acting on the object; and a processing device that is configured to perform the following: determining an estimated value for the spatial orientation of the object based on the detected rotational speed and a starting value for the spatial orientation; determining an acceleration component of the detect acceleration resulting from a rotational movement of the object, based on the detected rotational speed and a given distance of the second sensor from a rotational axis of the rotational movement; determining an acceleration component of the detected acceleration resulting from gravity; correcting the estimated value for the spatial orientation, taking into account the acceleration component resulting from gravity; and determining the distance of the second sensor from the rotational axis, based on an adjustment state of a fastening device, wherein the fastening device is adjustable, and wherein the fastening device is for fastening to a head of a user.

9. The device as recited in claim 8, wherein the first sensor is one of a one-axis micromechanical gyrosensor, a two-axis micromechanical gyrosensor, and a three-axis micromechanical gyrosensor.

10. The device as recited in claim 8, wherein the second sensor is one of a one-axis micromechanical acceleration sensor, a two-axis micromechanical acceleration sensor, and a three-axis micromechanical acceleration sensor.

11. A VR device, comprising:
- a fastening device for fastening to a head of a user;
- one of a visual output device and an acoustic output device;
- a device for determining a spatial orientation of an object, including:
  - a first sensor for detecting a rotational speed of the object;
  - a second sensor for detecting an acceleration acting on the object; and
  - a processing device that is configured to perform the following:
    - determining an estimated value for the spatial orientation of the object based on the detected rotational speed and a starting value for the spatial orientation;
    - determining an acceleration component of the detected acceleration resulting from a rotational movement of the object, based on the detected rotational speed and a given distance of the second sensor from a rotational axis of the rotational movement;
    - determining an acceleration component of the detected acceleration resulting from gravity; and
    - correcting the estimated value for the spatial orientation, taking into account the acceleration component resulting from gravity; and
- a sampling device for determining the distance of the second sensor from the rotational axis, based on an adjustment state of the fastening device, wherein the fastening device is adjustable.

* * * * *